United States Patent [19]

Holmes et al.

[11] Patent Number: 5,069,541
[45] Date of Patent: Dec. 3, 1991

[54] RIGID FRAMED SAFETY GOGGLES HAVING REPLACEABLE LENS

[75] Inventors: John A. Holmes, Hartesfinch, United Kingdom; Kazimierez J. Korny, Maughold, Isle of Man

[73] Assignee: Hellberg International Limited, Isle of Man

[21] Appl. No.: 386,615

[22] Filed: Jul. 31, 1989

[30] Foreign Application Priority Data

Aug. 2, 1988 [GB] United Kingdom ................ 8818345
Oct. 25, 1988 [GB] United Kingdom ................ 8824958

[51] Int. Cl.5 .............................................. G02C 1/00
[52] U.S. Cl. ...................................... 351/86; 351/57; 2/441
[58] Field of Search ................ 351/86, 47, 57; 2/429, 2/441

[56] References Cited

U.S. PATENT DOCUMENTS 3,031,674 5/1962 Ring ........................................ 2/441
4,799,781 6/1989 Weber .................................... 351/86

FOREIGN PATENT DOCUMENTS 67743 4/1974 Australia .
1048246 1/1952 France .
713057 9/1952 United Kingdom .

Primary Examiner—Paul M. Dzierzynski
Attorney, Agent, or Firm—Maksymonko & Slater

[57] ABSTRACT

A safety spectacle which allows for easy fitting and removal of lens parts to cater for individual requirements, including provision of single or twin lenses comprises a frame which is apertured to receive a lens or lenses of the spectacle and having abutment means over at least part of said aperturing which present retention faces to inside and outside surfaces of said lens or lenses, and clip means releasably locatably engageable with the frame and cooperable with the lens or lenses to retain the same in the spectacle frame in conjunction with the operation of the abutment means.

9 Claims, 2 Drawing Sheets

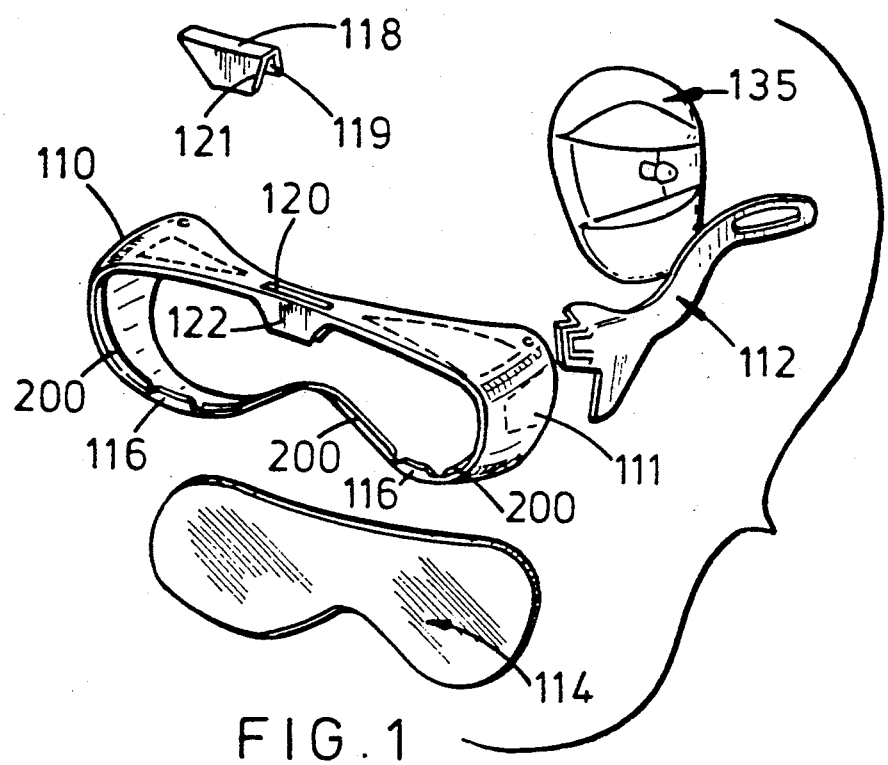
FIG. 1
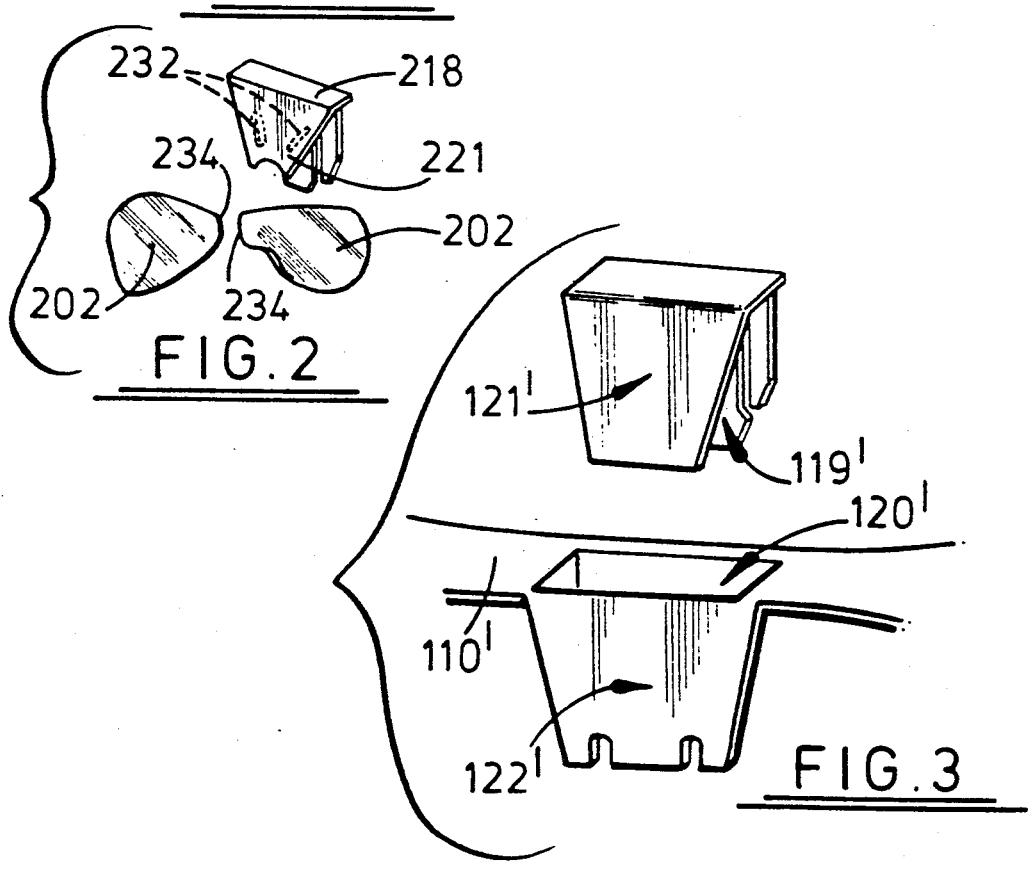
FIG. 2
FIG. 3

RIGID FRAMED SAFETY GOGGLES HAVING REPLACEABLE LENS

The present invention relates to spectacles, especially safety spectacles.

Existing safety spectacles are supplied already fitted with their lens part and do not allow for easy replacement of lens parts. This is disadvantageous because it is often the case that one of the lens part or the frame part may get damaged, but the design calls for replacement of the entire spectacles including arms in known designs. Furthermore existing spectacles come in two basic types—those accommodating a single (one piece) lens i.e. serving both eyes, or those having double lenses i.e. one for each eye as in conventional spectacles. The latter types can be provided with prescription lenses or with plane glass (known as plano lens), but the single lens type are only provided as a plano lens. The invention aims to provide a more versatile lens fitting system.

Accordingly there is provided a spectacle comprising a frame apertured to receive a lens or lenses of the spectacle and having abutment means over at least part of said aperturing and presenting retention faces to inside and outside surfaces of said lens or lenses, and clip means releasably locatably engageable with the frame and cooperable with the lens or lenses to retain same in the spectacle frame in conjunction with the operation of said abutment means.

More particularly the frame has a single aperture to accommodate either a single lens, with said abutment means providing retention to at least the lower boundary of the lens relative to each eye, and the clip means providing retention at an upper location, preferably utilising one clip disposed centrally above the nose bridge. Alternatively that single aperture can accommodate double lenses with the abutment means providing retention at a lower boundary of each lens and clip means again preferably centrally disposed to provide retention of both lenses. In a preferred construction the abutment means comprises a shoulder around the aperturing of the frame against which the rear face of the lens or lenses is pressed by the clip and additional retaining abutments for contacting and/or restraining the front face of the or each lens in the event of any forward movement. Those retaining abutments are conveniently disposed to the bottom edge and outer side of each lens opening.

In a preferred construction, a top rail part of the frame is apertured to receive a mating push-in part of the clip means, preferably in snap fitting manner, provided by such as resilient lugs. The clip further provides a face to restrain outward movement of the lens or lenses, and in the case of the clip for the double lens embodiment, preferably has ribs or such like which abut either the edges or the front of the lenses, or both to urge them into the frame aperturing for positive retention. In the former case those ribs preferably act in a wedging manner, being generally divergent to provide increased retention/wedging on insertion, and preferably also chamfered in a direction to urge the lenses rearwardly into the aperturing although it has been found that the shape of the lenses provides an automatic wedging action even where the ribs simply engage the front of the lenses. That engagement is advantageous for restraining positively to prevent rattling in use, but it could suffice for the ribs to be in closely spaced overlying relation.

The aforementioned clip retention system has the advantage that one design of frame can be used for both single and double lens design, providing economies of scale, and also making possible change from single to double lenses—of plano or prescription type as desired.

The present invention will now be described further, by way of example only, with reference to the accompanying drawings; in which:

FIG. 1 is an exploded perspective view of a safety spectacle with provision for fitting a single lens;

FIG. 2 is a perspective view showing an alternative clip and two lenses for use in place of the single lens of FIG. 1;

FIG. 3 is a larger detail perspective view of part of the spectacle frame and the clip;

Figure 4:
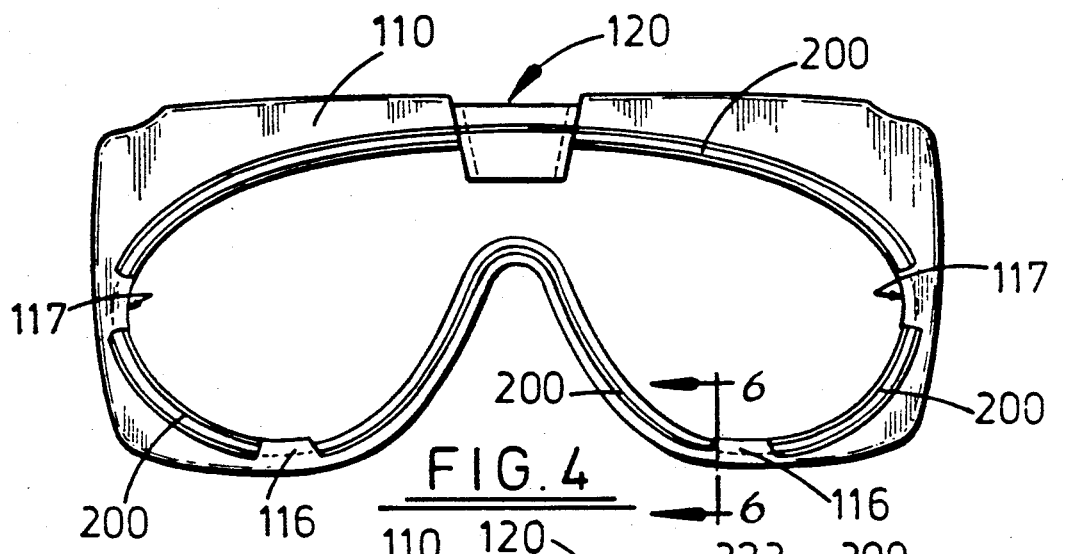
FIG. 4 is a front view of a spectacle frame showing more detail.

Referring firstly to FIG. 1 there is illustrated in exploded form a first embodiment of spectacle frame 110 formed as a moulding with slots shown dotted 111 for receiving side arms only one of which 112 is shown, employing resilient snap fastening. Also shown is an ear muff 135 for fixing to the end of the arm 112.

Figure 5:
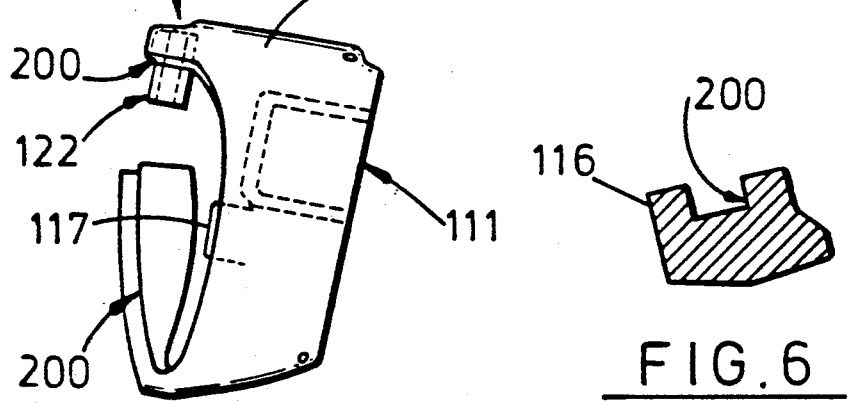
FIG. 5 is a side view of the frame of FIG. 4.
Figure 6:
FIG. 6 is a section on line 6—6 of FIG. 4.

A single lens is shown at 114 and is received within the frame 110 which provides a shoulder 200 (shown more clearly in FIGS. 4 to 6) against which the rear of the lens abuts around its periphery, with tabs 116 to provide lowermost retention, preferably also side tabs 117 as shown in FIG. 4. The tabs 116/117 provide for engagement with the front face of the lens, and act in cooperation with the shoulder 200 to provide retention of the lens. The abutment 200 is preferably broken at the position of the tabs 116, 117. FIG. 6 shows a section A—A illustrating how the lens fits between the abutment 200 and the tabs. Elsewhere the shoulder 200 being inset from the front of the frame provides an L-shaped lip surrounding the periphery of the lens. Positive location of the lens 114 is achieved by a generally U-shaped clip 118 one leg 119 of which is received (e.g. snap fittingly) in an opening 120 in the frame and the other 121 serves to trap the lens between it and a flange 122 of the frame 110 i.e. the lens is held against the outer face of flange 122, also against the abutment 200.

FIG. 3 illustrates an alternative and generally preferred embodiment of lens retention clip, essentially the same as that of FIG. 1, but having one limb with spring legs 119' engaging in the opening 120' with the lens being trapped between the leg 121' and the outer face of flange 122' of the frame 110.

Figure 7:
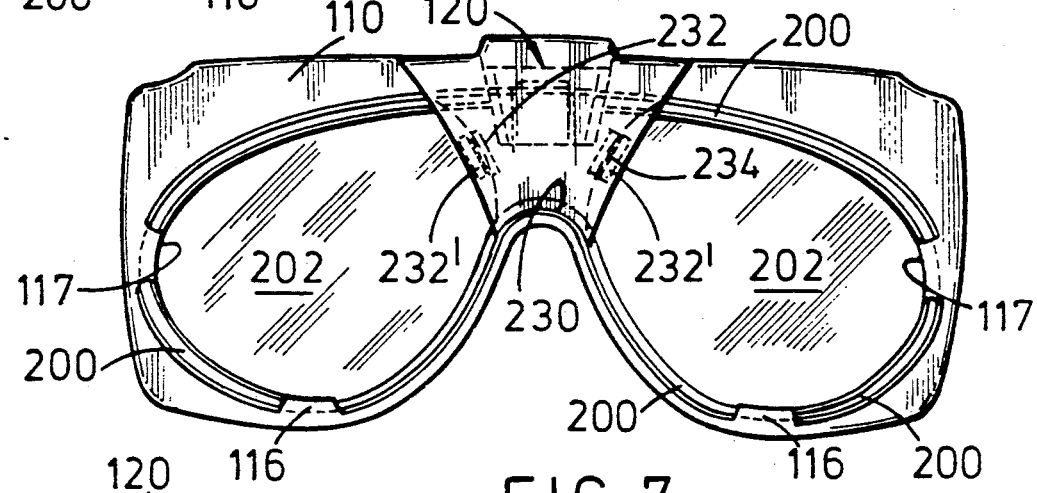
FIG. 7 is a front view of the frame of FIG. 4 fitted with the two lenses and clip of FIG. 2.

Referring now to FIGS. 2 and 7, here there is illustrated a pair of lenses 202, which are shaped for fitting into the aperture of frame 110 of the aforedescribed figures (and shown in FIG. 7) with their rear faces engageable against the abutment 200 (as with the single lens) and partially retained against forward movement by the tabs 116, 117. Retention of the two lenses in the frame is by way of a modified clip 218 having a rear limb of design corresponding to the clip of FIGS. 1 or 3, preferably as FIG. 3, with limbs 219 received snap fittingly in aperture 120, 120'.

The front limb 121 is larger, actually extending down to the nose bridge of the frame as at 230. On the rear side of the front limb 221 are two inclined lugs 232, shown in solid outline, actually set at an angle to engage with a respective edge 234 of each lens 202. These lugs act to urge the two lens rearwardly and diagonally downwardly to be retained between the abutment 200 and lugs 116, 117. The lugs 232 may be dispensed with and the front limb simply arranged to engage or overlie the front face of respective lenses 202 to hold same into its frame receiving well. That engagement may be by way of ribs 232', as shown in dotted outline.

It will be understood from the aforegoing description that the clip fitting of the single lens affords replacement of the lens or frame separate from the other, and that the ability to incorporate double lenses in one and the same frame enables a choice of plano or prescription lenses to be employed.

We claim:

1. A safety spectacle comprising a frame, lens means comprising a selected one of either twin lenses or a single lens, said lens means having inside and outside surfaces and peripheral edges, an aperture in the frame, the aperture defining a peripheral boundary configured to interchangeably receive either said twin lenses or said single lens said peripheral edges of the lens means being constrained by said peripheral boundary of the aperture, abutment means on at least part of said aperture providing retention faces to said inside surface and outside surfaces of said lens means, and centrally disposed clip means which is substantially U-shaped in cross-section and having a first limb by way of which it is releasably slidably locatably engagable with the frame, and having a second limb substantially parallel with the first and spaced therefrom and which overlies part of the outside surface of said lens means in its engaged position to retain said lens means in the aperture in conjunction with the operation of said abutment means, and wherein the retention faces to the inside and outside surfaces are so disposed as to allow insertion and removal of said lens means upon movement of said clip means from its engaged position.

2. The rigid framed protective eye wear of claim 1 in which rear and front abutment surfaces are spaced around the periphery of the rigid frame whereby an opening in the rear abutment surface is provided along and adjacent to each front abutment surface.

3. The rigid framed protective of claim 1 in which the rear abutment surface is defined along substantially the full length of the perimeter of the rigid frame aperture thereby providing enhanced goggle lens impact strength.

4. The rigid framed protective of claim 1 in which the lens abutment surfaces are recessed rearwardly from the rigid frame thereby improving goggle resistance to dirt and particle contamination.

5. The rigid framed eye wear of claim 1 in which said abutment means provides retention towards at least the lower boundary of the lens relative to each eye and the clip means provides retention at an upper location.

6. The rigid framed eye wear of claim 1 wherein the abutment means comprises a shoulder around the aperture of the frame against which the rear face of the lens is pressed by the clip means.

7. The rigid framed eye wear of claim 1 wherein the clip means engages the frame in a snap fitting manner.

8. The rigid framed eye wear of claim 7 wherein snap fitting is provided by a resilient leg having a retention abutment engaging with the frame and wherein release of the clip means is by actuation of the leg.

9. A safety spectacle comprising a frame, lens means comprising a selected one of either twin lenses or a single lens, said lens means having inside and outside surfaces and peripheral edges, an aperture in the frame, the aperture defining a peripheral boundary configured to interchangeably receive either said twin lenses or said single lens, said peripheral edges of the lens means being constrained by said peripheral boundary of the aperture, abutment means on at least part of said aperture providing retention faces to said inside surface and outside surfaces of said lens means, and centrally disposed clip means which is substantially U-shaped in cross-section and having a first limb by way of which it is releasably slidably locatably engagable with the frame, and having a second limb substantially parallel with the first and spaced therefrom and which overlies part of the outside surface of said lens means in its engaged position to retain said lens means in the aperture in conjunction with the operation of said abutment means, and wherein the retention faces to the inside and outside surfaces are so disposed as to allow insertion and removal of said lens means upon movement of said clip means from its engaged position, and in which the outside abutment means includes one or more lower retention fingers along the lower portion of the rigid frame and at least one side retention finger along each side of the frame, said side retention fingers being oriented at or below the maximum lateral width-wise extension of the lens whereby said side retention fingers do not obstruct the upward movement of the lens as required for the removal and replacement of the lens means.

* * * * *